United States Patent
Kim et al.

(10) Patent No.: US 11,357,989 B2
(45) Date of Patent: Jun. 14, 2022

(54) PACEMAKER LEAD FOR CERCLAGE PACING

(71) Applicants: June-Hong Kim, Busan (KR); Gi-Byoung Nam, Seoul (KR); Kyone Peter Park, Yangsan (KR)

(72) Inventors: June-Hong Kim, Busan (KR); Gi-Byoung Nam, Seoul (KR); Kyone Peter Park, Yangsan (KR)

( * ) Notice: Subject to any disclaimer, the term of this patent is extended or adjusted under 35 U.S.C. 154(b) by 183 days.

(21) Appl. No.: 16/685,918

(22) Filed: Nov. 15, 2019

(65) Prior Publication Data
US 2020/0179700 A1  Jun. 11, 2020

(51) Int. Cl.
| | | |
|---|---|---|
| A61B 17/34 | (2006.01) | |
| A61N 1/368 | (2006.01) | |
| A61N 1/372 | (2006.01) | |
| A61M 25/09 | (2006.01) | |

(52) U.S. Cl.
CPC ........ *A61N 1/3684* (2013.01); *A61B 17/3468* (2013.01); *A61N 1/37205* (2013.01); *A61B 2017/3433* (2013.01); *A61M 25/09* (2013.01); *A61N 1/36842* (2017.08); *A61N 1/36843* (2017.08)

(58) Field of Classification Search
CPC ... A61B 17/34; A61B 17/3468; A61B 19/201; A61B 2019/208; A61N 2001/0578; A61N 1/368; A61N 1/372; A61N 1/3684; A61N 1/36842; A61N 1/36843; A61N 1/37205
See application file for complete search history.

(56) References Cited

U.S. PATENT DOCUMENTS

| | | | |
|---|---|---|---|
| 5,476,498 A | * | 12/1995 | Ayers ................... A61N 1/0563 607/122 |
| D408,529 S | | 4/1999 | Hechel |
| D409,746 S | | 5/1999 | Hechel |
| 6,556,873 B1 | | 4/2003 | Smits |
| D496,728 S | | 9/2004 | Holsinger |

(Continued)

FOREIGN PATENT DOCUMENTS

| | | |
|---|---|---|
| EP | 3275390 A1 | 1/2018 |
| EP | 3653257 A1 | 5/2020 |

(Continued)

OTHER PUBLICATIONS

Pugazhendhi Vijayaraman, Pierre Bordachar, And Kenneth A. Ellenbogen, The Continued Search for Physiological Pacing: Where Are We Now?, J Am Coll Cardiol. Jun. 2017, 69 (25) 3099-3114.

*Primary Examiner* — Vi X Nguyen
(74) *Attorney, Agent, or Firm* — Justin Kim

(57) ABSTRACT

A pacemaker lead for cerclage pacing includes a lead fixing part including a fixing tip whose diameter becomes gradually smaller toward an end of a distal part thereof, a plurality of bipolar electrodes that come into close contact with heart muscle, in an outer circumference of the lead fixing part, and a guide wire insertion through hole through which a guide wire can be inserted thereinto, a lead body part configured to be extended to the lead fixing part, having a stylet insertion through hole formed therein, and a body fixing part formed in a bent shape so as to be fixed to an inner wall of the coronary sinus, and a stylet inserted into the stylet insertion through hole, enabling the pacemaker lead for cerclage pacing to be easily moved within the body of the patient.

10 Claims, 12 Drawing Sheets

(56) References Cited

U.S. PATENT DOCUMENTS

| | | |
|---|---|---|
| D497,509 S | 10/2004 | Nelson |
| D497,764 S | 11/2004 | Nelson |
| D627,064 S | 11/2010 | Appelbaum et al. |
| 8,052,659 B2 | 11/2011 | Ravenscroft et al. |
| D767,127 S | 9/2016 | Beer |
| D794,820 S | 8/2017 | Norell |
| D852,353 S | 6/2019 | Paul et al. |
| D861,156 S | 9/2019 | Greenhalgh et al. |
| 2002/0082614 A1 | 6/2002 | Logan et al. |
| 2003/0093104 A1 | 5/2003 | Bonner et al. |
| 2004/0143262 A1 | 7/2004 | Visram et al. |
| 2007/0051377 A1* | 3/2007 | Douk ................ A61B 17/0401 128/897 |
| 2008/0281312 A1 | 11/2008 | Werneth et al. |
| 2008/0287888 A1 | 11/2008 | Ravenscroft |
| 2010/0114140 A1 | 5/2010 | Chanduszko et al. |
| 2015/0148877 A1 | 5/2015 | Thakkar et al. |
| 2017/0150964 A1 | 6/2017 | Kim |
| 2020/0155229 A1 | 5/2020 | Kim et al. |

FOREIGN PATENT DOCUMENTS

| | | |
|---|---|---|
| EP | 3656327 A1 | 5/2020 |
| JP | 2011500209 A | 1/2011 |
| JP | 2017514553 A | 6/2017 |
| JP | 2020081870 A | 6/2020 |
| WO | 9808456 A1 | 3/1998 |
| WO | 0115618 A2 | 3/2001 |
| WO | 02094363 A2 | 11/2002 |

* cited by examiner

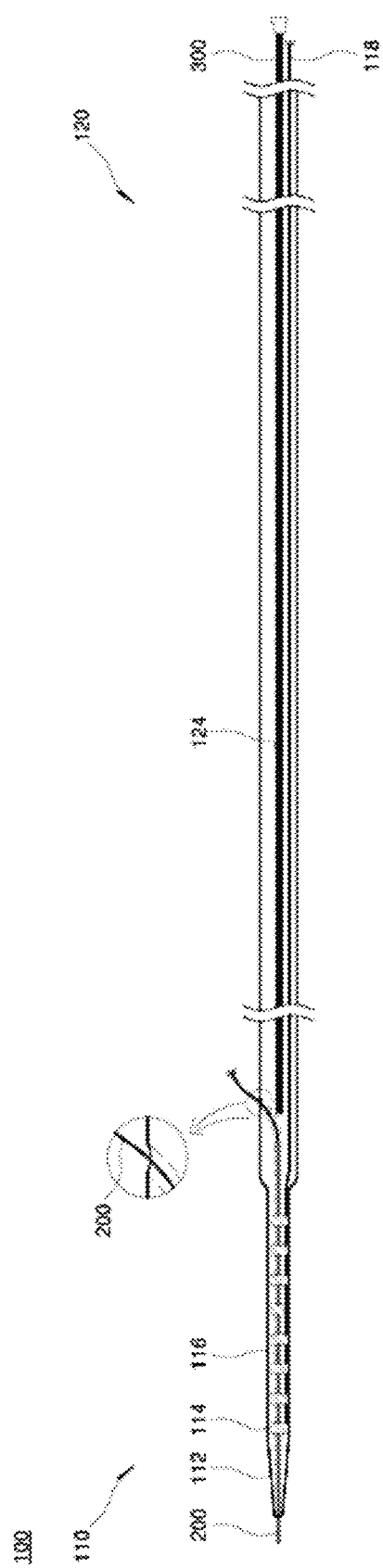

Septal vein

400

PACEMAKER LEAD FOR CERCLAGE PACING

CROSS REFERENCE TO RELATED APPLICATION

The present application claims priority to Korean Patent Application No. KR10-2018-0140401, filed 15 Nov. 2018, the entire content of which is incorporated herein for all purposes by reference.

BACKGROUND OF THE INVENTION

Field of the Invention

The present invention generally relates to a pacemaker lead for cerclage pacing. More particularly, the present invention relates to a pacemaker lead for cerclage packing, which moves along the coronary sinus and reaches the interventricular septum, enabling efficient electrical transmission as the pacemaker lead is close to the His bundle, and includes a stylet, having improved pushability so that the lead can be easily moved in a patient's body.

Description of the Related Art

An artificial pacemaker was first introduced in 1958 by Furman S. and Robinson G., etc. Since then, the pacemaker has been used as an important treatment of a bradyarrhythmia patient. Recently, the artificial pacemaker has been used as an important treatment of arrhythmia diseases such as complete auriculoventricular block or high degree auriculoventricular block, or sick sinus syndrome accompanying symptoms. Treatment by the pacemaker is a treatment method to artificially generate electrical impulses by use of the artificial pacemaker when electric stimulus of the heart does not normally flow.

FIG. 1 shows a cardiac conduction system. Referring to FIG. 1, electrical conduction of the heart is made by passing through an atrioventricular node from a sinoatrial node within an atrium, and through Purkinje fibers in a right bundle and a left bundle divided from the His bundle in a ventricle.

In an electrocardiogram ("ECG"), the QRS complex is generated by a depolarization process of a ventricular muscle, and a Q wave refers to a first downward deflection immediately following a P wave, an R wave refers to a first upward deflection, and an S wave refers to a downward deflection following the R wave. A width of QRS means a period of time during which electricity is being conducted to the entire ventricles of the heart from the His bundle. In a normal state, the width of QRS is about 0.12 seconds (about 90 ms). In this regard, if the width of QRS is more than 0.12 seconds (120 ms), this suggests intraventricular conduction disturbance. As the electric conduction time is long, the QRS width is widened, but if the electric conduction time is short, the QRS width is narrowed. The wide QRS causes ventricular desynchronization due to failure to unify motions of the ventricles, bringing a side effect that the ventricular function is lost.

That is, if electric stimulus is applied to a point close to the His bundle located in the interventricular septum, the electric conduction time is shortened and a narrow QRS can be obtained. Accordingly, the electric stimulus can be effectively transmitted.

However, it is difficult to accurately find the His bundle located in the interventricular septum during an operation. Although the His bundle is found and a pacemaker lead is fixed to the His bundle, the pacing threshold is high, so a defect that the battery life of the pacemaker is shortened is produced.

In this regard, a number of various methods to find a position to fix a pacemaker lead, to replace the His bundle, have been researched. A paper, JACC Vol. 69, No. 25, Jun. 27, 2017, p. 3099-3114 (Non-patent Literature 1), arranges various methods associated with positions to fix pacemaker leads developed according to a conventional art. FIG. 2 is a picture attached to the said paper, showing various positions at which the pacemaker leads developed according to a conventional art are fixed.

First, in a method to fix the pacemaker lead at a right ventricular apex ("RVA"), a QRS of about 172 ms was measured, showing a wider QRS than a QRS numerical value of the His bundle, exhibiting a result that heart failure ("HF") or atrial fibrillation was caused, thereby further aggravating a patient's condition.

A method to fix the pacemaker lead at a right ventricular outflow tract ("RVOT") or a right ventricular septal ("RV septal") exhibited a QRS value of about 165 ms, which is an excellent value, as compared with the method to fix the pacemaker lead at the RVA. However, like the method to fix the pacemaker lead at the RVA, heart attack, atrial fibrillation, etc. were caused. Also, the operations were successful only for about 66% of the patients, and the operations exhibited difficulty.

As an alternative, a method to fix the lead at a left ventricle ("LV") has been researched. The method to fix the lead at the LV includes fixation of the lead at an external membrane of the LV and fixation of the lead at an internal membrane of the LV. When the lead is fixed at the external membrane of LV rather than at the external membrane of LV, excellent physiological electrical activation (narrow QRS) was exhibited, indicating that efficient electric transmission is available. However, according to a method to fix the lead at the LV, the pacemaker lead pierces into a thin membrane between the right atrium and the left atrium to enter into the LV, and thus, this method has a problem of making an operation difficult.

US Patent Application Publication Nos. 2010/0298841 and 2013/0231728 address a method for positioning a pacemaker lead forcibly in the interventricular septum by allowing the lead to directly pierce into the right ventricle toward the left ventricle. This method covers a method of stimulating the left interventricular septum rather than the right interventricular septum, which can realize a narrower QRS (145 ms) than stimulating the right interventricular septum, having an effect to replace a cardiac resynchronization therapy (CRT). However, the method disclosed by these patent applications requires very high invasion, causing artificial loss of the interventricular septum between the left ventricle and the right ventricle. In this regard, a risk that adjacent tissues are torn during operation is very high, and a risk that an embolism due to air or blood clot, etc. is generated is also very high. Also, available access is limited to middle or an apex of the ventricle, not to the base of the ventricle, as a desirable portion. Accordingly, significant risks and limitations are implied in the above-described method.

Recently, a method to complement the defects of the above-described patent applications by fixing the lead has been researched. The method uses a screw-type lead rather than to perforate a bore from the right ventricle to the left ventricle and fixes the lead by rotating a screw until the lead reaches the left interventricular septum from the right interventricular septum. However, this method is also highly liable to damage other tissues such as tricuspid tissues, and a defect that it is difficult to move the lead close to the His bundle still remains.

Therefore, there is a demand for researches for a pacemaker lead that can effectively transmit electrical stimulus similar to the His bundle and transmit the electric stimulus in a safe and simple manner.

The foregoing is intended merely to aid in the understanding of the background of the present invention, and is not intended to mean that the present invention falls within the purview of the related art that is already known to those skilled in the art.

DOCUMENTS OF RELATED ART

Patent Documents (Patent Document 1) US 2010/0298841 A1 published on Nov. 25, 2010; and
(Patent Document 2) US 2013/0231728 A1 published on Sep. 5, 2013

Non-Patent Documents (Non-patent Document 1) "The Continued Search for Physiological Pacing", Journal of the American College of Cardiology, Vol. 69, No. 25, May 3, 2017).

SUMMARY OF THE INVENTION

Accordingly, the present invention has been made keeping in mind the above problems occurring in the related art, and an object of the present invention is to provide a pacemaker lead fixed at the base of the interventricular septum close to the His bundle, to effectively transmit electrical stimulus to the heart.

Another object of the present invention is to provide a pacemaker lead which can find an optimal electrical conduction position according to each patient by measuring electrocardiograms (ECGs) at several positions of the interventricular septum, without replacing the lead.

Still another object of the present invention is to provide a pacemaker lead which can be moved in the body of a patient in a simple manner, without requiring any other device, and whose position as fixed is not changed according to a motion of the heart.

The present invention is not limited to the above-described objects, and another objects not mentioned above can be clearly appreciated by a person having ordinary knowledge in the art to which the present invention pertains, from the description of the invention as described below.

In order to achieve the above objects, according to one aspect of the present invention, there is provided a pacemaker lead for cerclage pacing, the pacemaker lead including: a lead fixing part including a fixing tip whose diameter becomes gradually smaller toward an end of a distal part thereof, a plurality of bipolar electrodes which come into close contact with a heart muscle in an outer circumference of the pacemaker lead, and a guide wire insertion through hole through which a guide wire can be inserted thereinto; a lead body part configured to be extended to the lead fixing part, having a stylet insertion through hole formed therein, and a body fixing part in a bent form so as to be fixed to an inner wall of the coronary sinus; and a stylet inserted into the stylet insertion through hole, enabling the pacemaker lead for cerclage pacing to be easily moved within the body of a patient.

In an embodiment, a first end of the guide wire insertion through hole may be provided at the end of the distal part of the fixing tip, and a second end of the guide wire insertion through hole may be provided at a lateral side of the lead body part.

In another embodiment, the first end of the guide wire insertion through hole may be provided at the end of the distal part of the fixing tip, and the second end of the guide wire insertion through hole may be provided at a lateral side of the lead fixing part.

In a further embodiment, the first end of the guide wire insertion through hole may be provided at the end of the distal part of the fixing tip, and the second end of the guide wire insertion through hole may be provided at an end of a proximal part of the lead body part.

The lead fixing part may be formed of French size (Fr) 2 to 5.5, so as to easily pierce into the heart muscle and to be then fixed thereto, and the bipolar electrodes may include at least two bipolar electrodes, and may be configured such that a distance between the electrodes is 2 mm to 10 mm, electric signals of the electrodes can be respectively measured, and electrical transmission thereof is enabled.

Also, an end of a distal part of the stylet insertion through hole may be configured in a closed manner and positioned on the same vertical line as an end of a proximal part of the guide wire insertion through hole.

The body fixing part may be ductile so as to be spread in a straight line when the stylet is inserted into the stylet insertion through hole, the body fixing part may be elastic so as to be restored to an originally bent shape when the stylet is removed, and the body fixing part may include a plurality of ductile wires provided on a side wall thereof, thus increasing a fixing force.

Also, the stylet may be configured to become stronger from a distal part toward a proximal part thereof, and the stylet may have a diameter which becomes smaller toward an end of the distal part thereof.

According to the present invention, the pacemaker lead is fixed at the base of the interventricular septum close to the His bundle, thus efficient electrical transmission is enabled.

According to the present invention, as the pacemaker lead includes a plurality of electrodes, electrical stimulus can be checked at several positions, and a position to transmit electrical stimulus can be changed for each patient, without requiring a re-operation.

According to the present invention, as the stylet is inserted into the lead body part, the pacemaker lead can be easily inserted into and moved in a blood vessel, without requiring any other device when the stylet is moved in the body of a patient.

According to the present invention, the lead fixing part is thin about Fr 4, and the lead fixing part includes a fixing tip having a diameter of an end thereof that becomes smaller, serving to easily pierce into the interventricular septum.

According to the present invention, the pacemaker lead can be inserted and fixed in a stable manner, without damaging any other tissues in the heart.

BRIEF DESCRIPTION OF THE DRAWINGS

The above and other objects, features and other advantages of the present invention will be more clearly understood from the following detailed description when taken in conjunction with the accompanying drawings, in which:

FIG. 4A is a perspective sectional view of the lead according to an exemplary embodiment of the present invention;

DETAILED DESCRIPTION OF THE INVENTION

Figure 1:
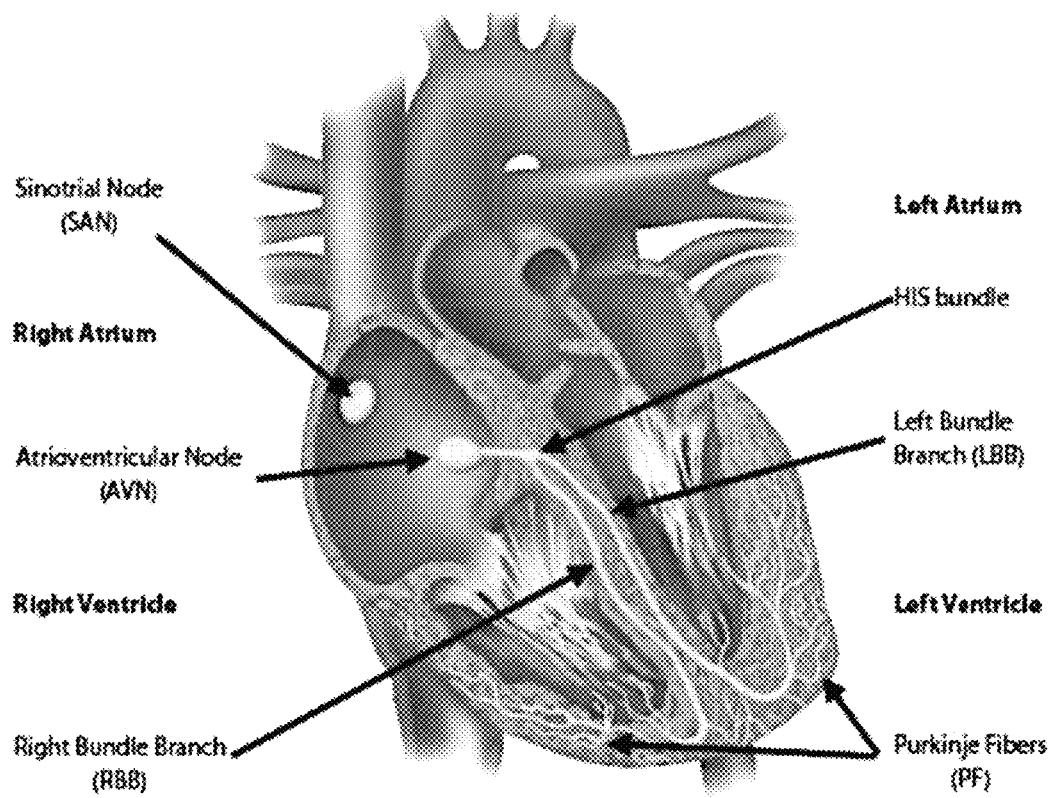
FIG. 1 is a view showing a cardiac conduction system.
Figure 2:
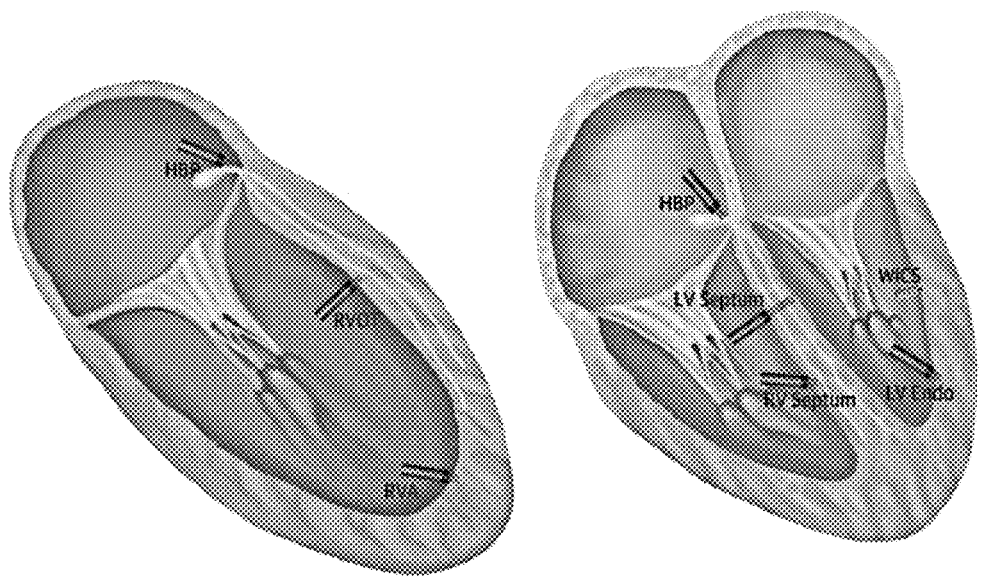
FIG. 2 is a view showing a position at which a pacemaker lead developed according to a conventional research is fixed.

Hereinbelow, exemplary embodiments of the present invention will be described in detail with reference to the accompanying drawings. Throughout the drawings, the same reference numerals will refer to the same or like parts.

Figure 3:
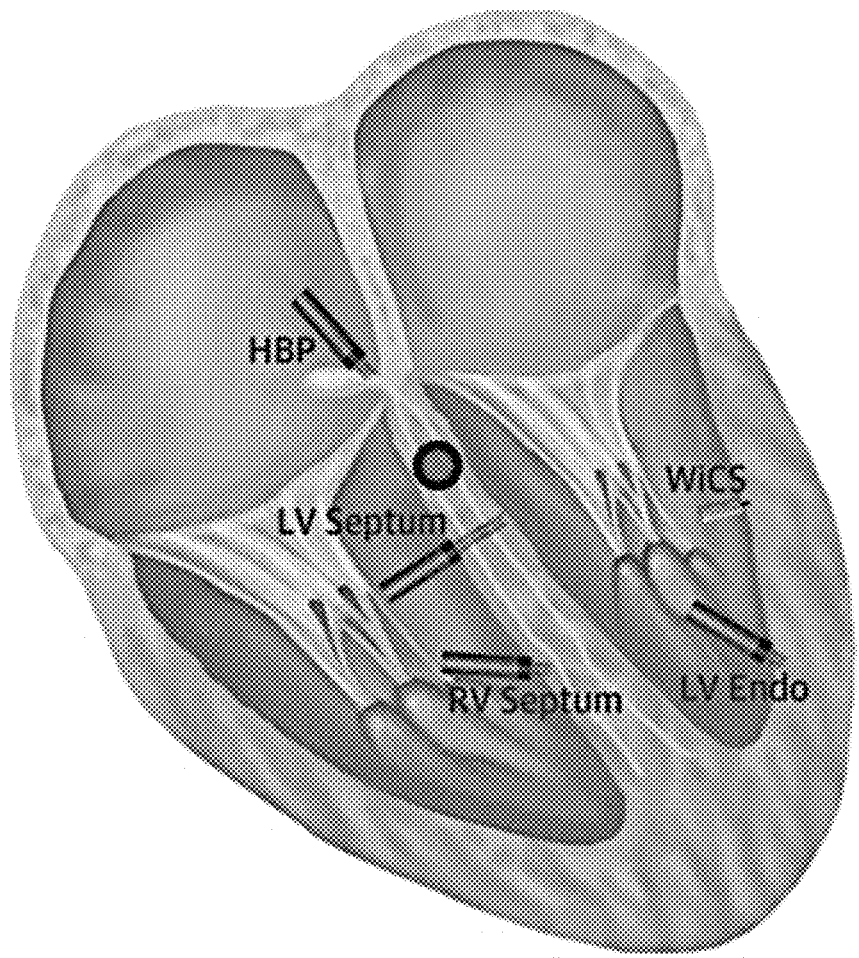
FIG. 3 is a view showing a position at which a lead according to the present invention is fixed at the interventricular septum.

FIG. 3 is a view showing a position at which a lead according to the present invention is fixed at the interventricular septum.

According to the present invention, a pacemaker lead is inserted into the body of a patient along the same passage as the passage through which to enter into the body of the patient, in "a tissue protection device for mitral valve membrane cerclage procedure" invented by the inventors of the present invention, which was applied for under Korean Patent No. 10-1563172.

As described above, the pacemaker lead according to the present invention is inserted into a coronary sinus and then moves along the coronary sinus to reach the interventricular septum. A position at which an end of the lead is fixed is a basal interventricular septum between the His bundle (HBP) and the left ventricular (LV) septum, as indicated in a red circle by FIG. 3.

Where the pacemaker lead is fixed at the His bundle (HBP), as a narrow QRS can be obtained, it is possible to reduce the electrical conduction time, enabling efficient electrical transmission. However, it is difficult to locate an accurate position of the His bundle positioned in the interventricular septum during an operation, and a pacing threshold is high even though the pacemaker lead is fixed at the His bundle. In this regard, there is a problem in reducing a battery life of the pacemaker lead.

Where the pacemaker lead is fixed at the left ventricular (LV) septum, a narrower QRS than to stimulate the right ventricular (RV) septum can be realized, having an effect to replace the cardiac resynchronization therapy (CRT). However, this is a very invasive treatment because this treatment requires to perforate a bore from the right ventricle to the left ventricle, so as to insert the lead into the right ventricle and the left ventricle. In this regard, this method is highly liable to damage other tissues such as the tricuspid valve, etc.

According to the present invention, a portion at the lead is fixed (indicated by a red circle in FIG. 3) is close to the His bundle rather than to the left ventricular (LV) septum, having an excellent efficiency of electrical conduction, the lead may be fixed without perforating the interventricular septum from the right ventricle to the left ventricle, like the lead located at the left ventricular (LV) septum, and the lead may be fixed, without damaging other tissues such as the tricuspid valve.

Also, it is difficult to find a position at the His bundle during an operation. However, the lead according to the present invention enters along the coronary sinus tube to be fixed, a position to fix an end of the lead can be more easily found.

As described above, the pacemaker lead for cerclage pacing according to the present invention complements defects of a device to fix an end of the lead developed according to a conventional art at the His bundle, and a device to fix the end of the lead at the left ventricle (LV) septum, and maintains all the advantages of these conventional devices.

FIG. 4A is a perspective sectional view of the lead according to an exemplary embodiment of the present invention.

Referring to FIG. 4A, the lead 100 according to an exemplary embodiment of the present invention includes a lead fixing part 110 and a lead body part 120.

The lead 100 is formed with a single catheter or a cylindrical tube, and the materials thereof may include rubber materials, synthetic materials, or a mixture of polyurethane and silicone, which are soft and ductile.

The lead fixing part 110 constitutes a portion to pierce into the heart muscle to be then fixed and to transmit electrical stimulus. A guide wire insertion through hole 116 through which a guide wire 200 can be inserted is famed inside the leading fixing part 110.

The lead fixing part 110 includes a fixing tip 112 whose diameter is gradually tapered toward to an end of a distal part thereof, and a plurality of electrodes 114 coupled to an outer circumference of the lead fixing part 110, to come into close contact with the heart muscle.

The fixing tip 112 is configured to easily pierce into the heart muscle for each insertion. According to an exemplary embodiment of the present invention, the fixing tip 112 is formed to have a diameter that gradually becomes smaller (that is, in a tapered form) toward an end of the distal part thereof.

Also, the lead fixing part 110 has a size of 2 to 5.5 French sizes (Fr), which is configured to be thin so as to easily pierce into the heart muscle. The size of 4 Fr is preferable, but the lead fixing part 110 may also be configured to have a size of 5.1 Fr, 5.2 Fr, etc.

The electrode 114 is a bipolar electrode, coupled to an outer circumference of the lead fixing part 110, and the electrode 114 is provided in plural. A plurality of the electrodes 114 are coupled to the respective one ends of a plurality of electrode wires 118, and the respective other ends of the plurality of electrode wires 118 are connected to the pacemaker. Measurement of respective electrical signals by the electrodes 114 in plural is enabled, and transmission of electrical stimulus is also enabled.

For example, if the lead fixing part 110 includes five electrodes, the signals of the five electrodes are respectively measured, on the basis of which an optimal position is found based on each patient. Then, stimulus of a positive electrode and a negative electrode, or stimulus of a negative electrode and a positive electrode may be provided to a first electrode and a third electrode respectively, or stimulus of a positive electrode and a negative electrode, or stimulus of a negative electrode and a positive electrode may be provided to a fourth electrode and a fifth electrode respectively.

The lead 100 according to the present invention is capable of selecting electrodes in a position suitable for each patient for electrical transmission, as exemplified above.

A plurality of the electrode wires 118 can be inserted in a straight line onto a lateral wall of the lead body part 120. It is also possible to insert the plurality of electrode wires 118 in a helical form onto the lateral wall of the lead body part 120.

The plurality of electrodes 114 are mounted at intervals of 2 mm to 10 mm. More preferably, the electrodes 114 are mounted at intervals of 2 mm to 3 mm.

As the lead 100 according to the present invention includes a plurality of bipolar electrodes 114, an optimal position to transmit electrical signals, which differs from each patient, is detected and the electricity is transmitted to an electrode close to the detected position, thereby enabling more efficient transmission of electrical stimulus. Accordingly, it is possible to adjust a position for the electrical transmission depending upon a patient, without a re-operation to change a position of the lead.

One end of the guide wire insertion through hole 116 is formed at an end of the distal part of the fixing tip 112, and the other end of the guide wire insertion through hole 116 is formed on a lateral side of the lead body part 120. The guide wire 200 is inserted into an end of the guide wire insertion through hole 115 formed at the fixing tip 120 and passes through the other end of the guide wire insertion through hole 116 formed at the lateral side of the lead body part 120.

According to this, the guide wire 200 can be inserted and removed more quickly than a method that the guide wire passes through the entire lead body part 120.

Wires of synthetic resins such as nylon or metal materials (stainless steel, a metal coated with nylon), etc. may be used for the guide wire 200. A wire formed by twisting plural thin wires may also be used. Preferably, the guide wire having a diameter of 0.014 inches is used.

Also, the guide wire 200 provides a passage along which the lead 10 moves in the body of a patient, and pushability is enhanced when the guide wire 200 is inserted into the lead fixing part 110 and the lead fixing part 110 moves in the body of the patient.

The lead body part 120 is configured to be extended from an end of a proximal part of the lead fixing part 110, having a diameter larger than the lead fixing part 110. As the lead body part 120 is located within the coronary sinus having a blood vessel that has a relatively large inner diameter, it is possible that the lead body part 120 has a larger diameter than the lead fixing part 110. The lead body part 120 includes a body fixing part 122 and a stylet insertion through hole 124.

The stylet insertion through hole 124 into which a stylet 300 is inserted is formed inside the lead body part 120, and the stylet insertion through hole 124 does not communicate with the guide wire insertion through hole 115 because the end of the distal part thereof is closed.

The end of the distal part of the stylet insertion through hole 124 is located on the same vertical line as the end of the proximal part of the guide wire insertion through hole 116.

It is possible that the end of the distal part of the stylet insertion through hole 124 may be formed at the distal part of the guide wire insertion through hole 115 rather than on the vertical line of the end of the distal part of the guide wire insertion through hole 116, thereby allowing the stylet insertion through hole 124 to be formed partially in parallel with the guide wire insertion through hole 120 within the lead body part 120.

Accordingly, when after the stylet 300 is inserted into the stylet insertion through hole 120, they are pushed by an operator to move the lead 100 in the body of the patient without being bent.

The stylet 300 which is to provide additional solidity for adjustment of direction when a catheter, a lead, etc. is moved to desired positions in the body of the patient. The stylet 300 may be constructed with the same material as the guide wire 200, and has the same thickness as or wider thickness than the guide wire 200.

The stylet 300 is formed to be more solid toward the proximal part from the distal part thereof. A material of the distal part is ductile so as to be more movable than that of the proximal part, so that the stylet 300 can be easily moved along the curved blood vessel in the body of the patient, and a material of the proximal part is solid so as to receive the force pushed by the operator.

Accordingly, as the lead 100 formed of a ductile material cannot easily move to a position desired by the operator when the lead 100 moves in the body of the patient or in the blood vessel, the lead 100 requires another device to help movement thereof. However, the lead 100 according to the present invention requires no other device as the stylet 300 is inserted into the stylet insertion through hole 124, enhancing pushability of the lead 100, and the lead 100 can be easily inserted into the coronary sinus tube to move toward the interventricular septum.

Figure 4B:
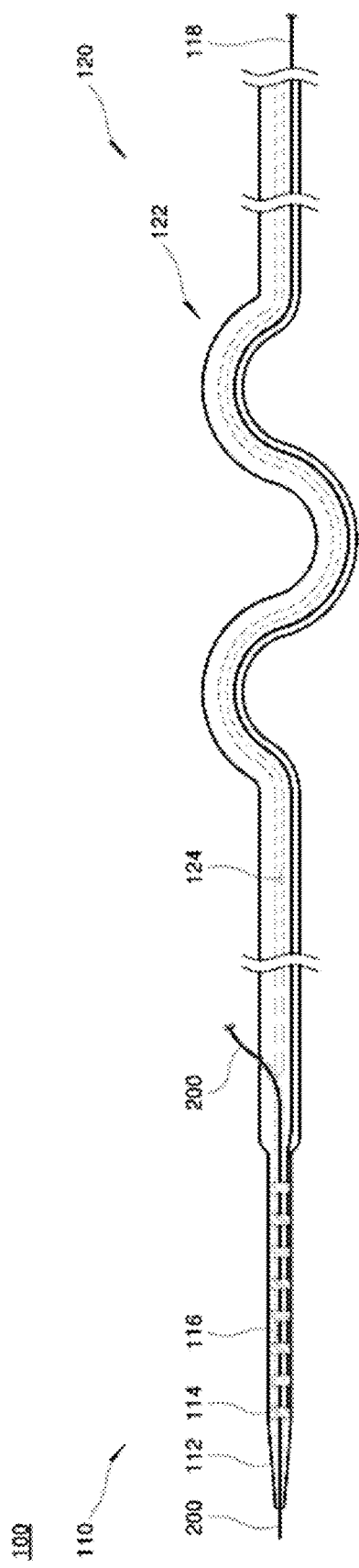
FIG. 4B is a perspective sectional view showing that a fixing part is deformed by removing a stylet from the lead according to an exemplary embodiment of the present invention.

FIG. 4B is a perspective sectional view showing that a body fixing part is deformed by removing a stylet from the lead according to an exemplary embodiment of the present invention.

In the lead body part 120, a body fixing part 122 is formed at a portion located in the coronary sinus, and the body fixing part 122 is formed after bending one side of the lead body part 120 in a spiral or wave form, etc. and heating the bent side. FIG. 4B shows the body fixing part 122 in a wave form, but the body fixing part 122 may be modified in various forms to press the inner wall of the coronary sinus.

As the body fixing part 122 is formed by heating one side of the soft lead body part 120, the body fixing part 122 is elastic so as to be spread and restored to the portion bent in a spiral or wave form according to the movement of the heart, thereby being capable of absorbing impact applied to the lead fixing part 110.

The body fixing part 122 is ductile so as to be spread in a straight line when the stylet 300 is inserted into the stylet insertion through hole 124 and also elastic so as to be restored to an originally bent shape when the stylet 300 is removed.

Accordingly, after the lead 100 is prepared in a straight line outside the body of the patient by inserting the stylet 300 into the lead body part 120 at which the body fixing part 122 is formed, the lead 100 enters into the body of the patient. If the stylet 300 is removed outside the body of a patient after the lead fixing part 110 is fixed at the interventricular septum, the body fixing part 122 is restored to the originally bent shape to be then fixed at the coronary sinus.

Figure 4C:
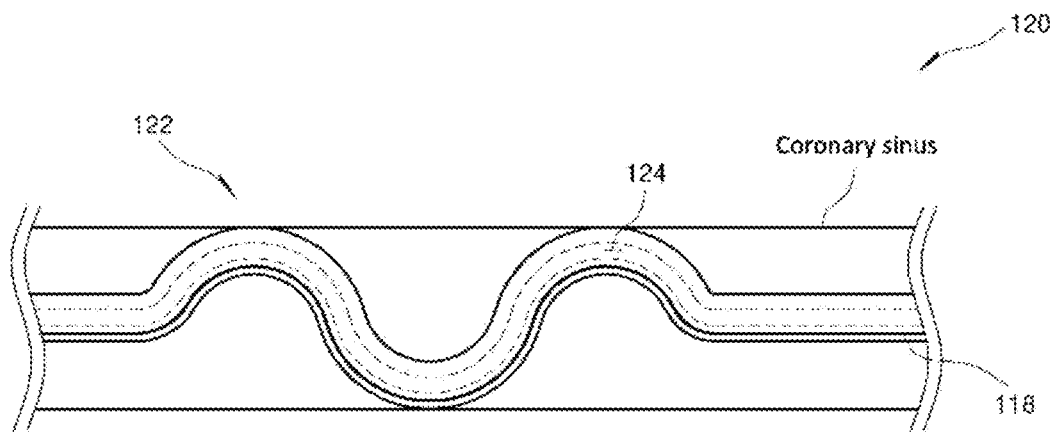
FIG. 4C is a view showing a state where a lead body part according to an exemplary embodiment of the present invention is fixed at a coronary sinus.

FIG. 4C is a view showing a state that a lead body part according to an exemplary embodiment of the present invention is fixed at a coronary sinus. As shown therein, the body fixing part 122 comes into contact with two or three points on the inner wall of the coronary sinus, thereby slightly pressing the coronary sinus. The degree that the lead body part 120 presses the coronary sinus is so slight as not to damage the coronary sinus. The coronary sinus is pressed with a force to such a degree that the lead body part 120 can be fixed stably in the body of the patient. Due to this, the lead 100 is stably fixed without being deviated from the originally fixed position despite movement of the heart.

Figure 4D:
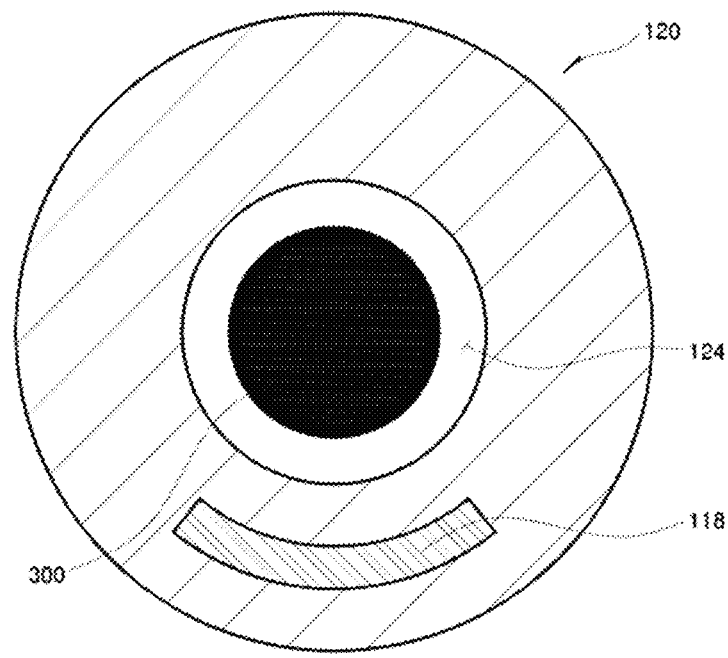
FIG. 4D is a sectional view of the lead body part according to an exemplary embodiment of the present invention.

FIG. 4D is a sectional view of the lead body part according to an exemplary embodiment of the present invention.

As shown in FIG. 4D, the stylet insertion through hole 124 is formed inside the lead body part 120. The stylet 300 is inserted into the stylet insertion through hole 124, and the electrode wires 118 are inserted onto the lateral side of the lead body part 120.

Figure 5A:
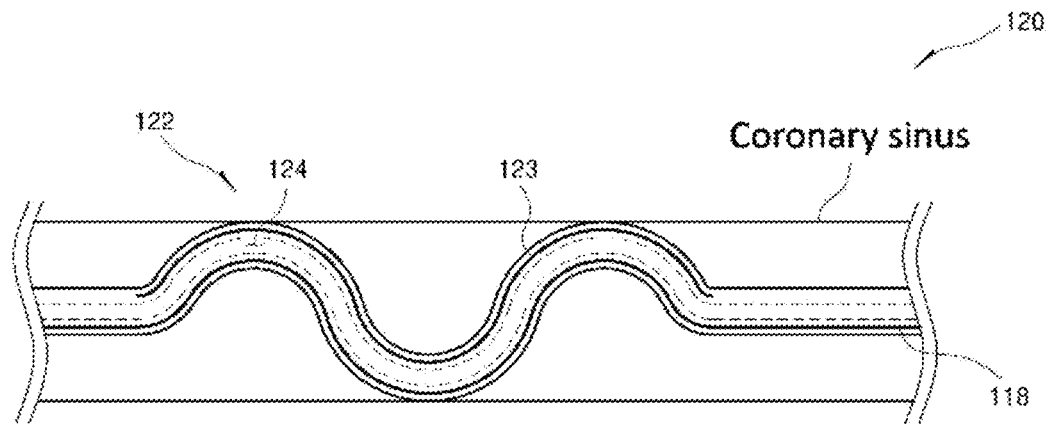
FIG. 5A is a perspective sectional view of a body fixing part according to an exemplary embodiment of the present invention.
Figure 5B:
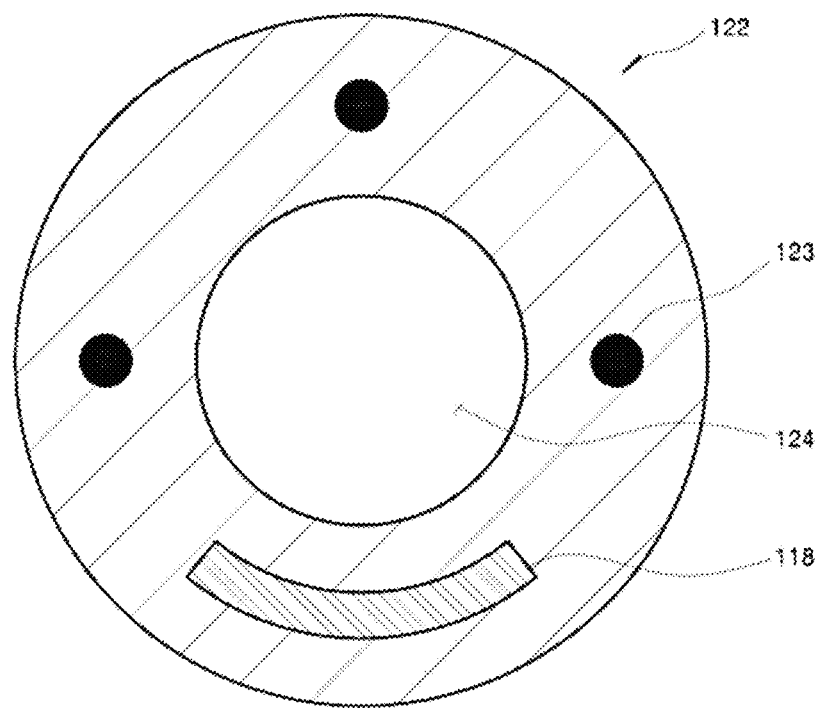
FIG. 5B is a perspective sectional view of a fixing part according to an exemplary embodiment of the present invention.

FIG. 5A is a perspective sectional view of a body fixing part according to an exemplary embodiment of the present invention, and FIG. 5B is a perspective sectional view of a body fixing part according to an exemplary embodiment of the present invention.

Referring to FIGS. 5A and 5B, another body fixing part 122 according to an exemplary embodiment of the present invention includes a reinforcing means 123. The reinforcing means 123 is formed of a single ductile wire or a plurality of ductile wires.

The reinforcing means 123 is to reinforce the fixing power when the body fixing part 122 is locked to the coronary sinus, being directed to minimize movement of the lead 100 according to the heart beat when the body fixing part 122 is bent to thereby come into contact with the coronary sinus to fix the lead 100.

As the reinforcing means 123 is a ductile wire, the body fixing part 122 is spread to be in a straight line if the stylet 300 is inserted into the stylet insertion through hole 124, and is deformed to be bent back if the stylet 300 is removed.

Figure 6:
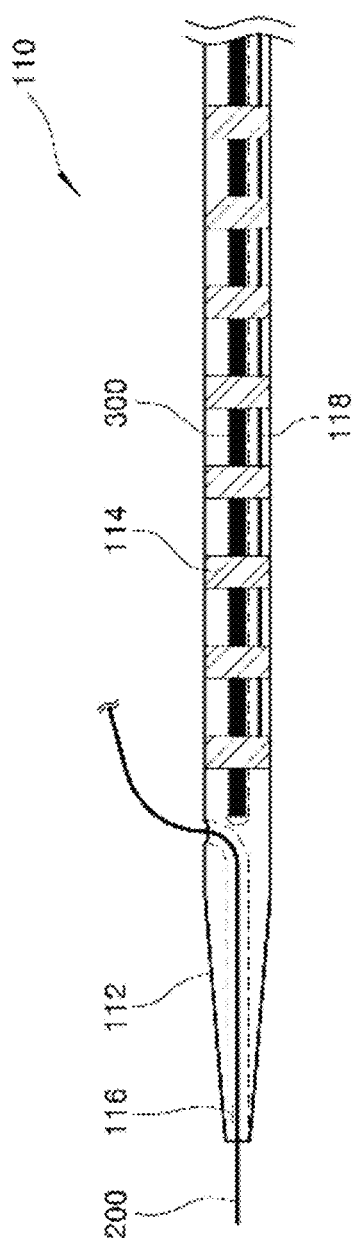
FIG. 6 is a perspective sectional view of a guide wire insertion through hole according to another exemplary embodiment of the present invention.

FIG. 6 is a perspective sectional view of a guide wire insertion through hole according to another exemplary embodiment of the present invention.

Referring to FIG. 6, the guide wire insertion through hole 116 according to another exemplary embodiment of the present invention has one end formed at an end of the distal part of the fixing tip 112 and the other end formed at a lateral side of the lead fixing part 110.

The other end of the guide wire insertion through hole 116 is formed at the distal part rather than at a point to which the electrode 114 is coupled, and the stylet insertion through hole 124 is elongated up to the inside of the lead fixing part 110. Preferably, one end of the stylet insertion through hole 124 is formed at the same straight line as the other end of the guide wire insertion through hole 116. Accordingly, the stylet 300 is inserted into the stylet insertion through hole 123 formed up to the lead fixing part 110, thereby enhancing pushability of the lead 100. Also, the guide wire 200 may be inserted and removed more quickly than a configuration wherein the guide wire 200 passes through the entire lead body part 120.

At this time, the stylet 300 has a diameter tapered toward the distal part of the stylet 300 so as to be inserted into the lead fixing part 110.

Figure 7A:
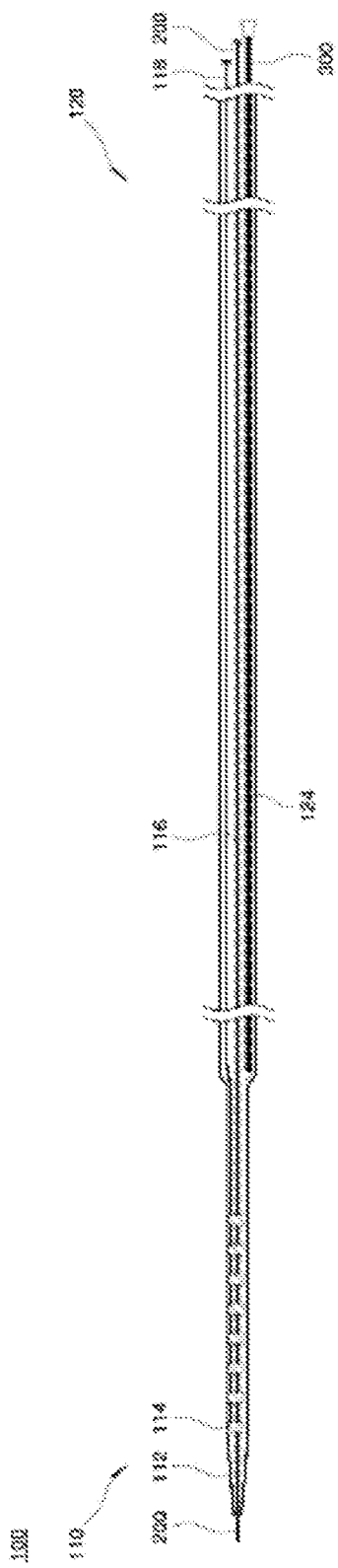
FIG. 7A is a perspective sectional view of a guide wire insertion through hole according to a further other exemplary embodiment of the present invention.

FIG. 7A is a perspective sectional view of a guide wire insertion through hole according to a further other exemplary embodiment of the present invention.

One end of the guide wire insertion through hole 116 is formed at an end of the distal part of the fixing tip 112 and the other end thereof is formed at an end of the proximal part of the lead body part 120.

According to a guide wire insertion through hole of a further other exemplary embodiment of the present invention, if the guide wire 200 is inserted into the guide wire insertion through hole 116, one side of the guide wire 200 passes out of the end of the proximal part of the lead body part 120.

Figure 7B:
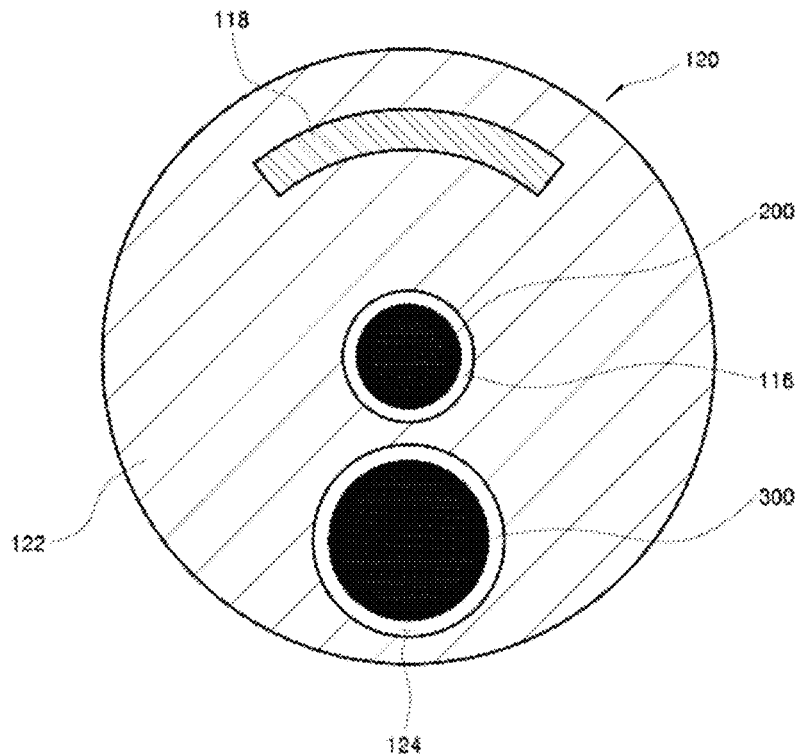
FIG. 7B is a sectional view of the lead body part according to another exemplary embodiment of the present invention.

FIG. 7B is a sectional view of the lead body part according to another exemplary embodiment of the present invention. In other words, FIG. 7B shows a section of the lead body part 120. According to the lead body part 120 according to a further other exemplary embodiment of the present invention, the stylet insertion through hole 124 and the guide wire insertion through hole 116 are formed in parallel with each other inside the lead body part 120. The electrode wire 118 is coupled to the lead body part 120 along the lateral wall of the lead body part 120.

Figure 8:
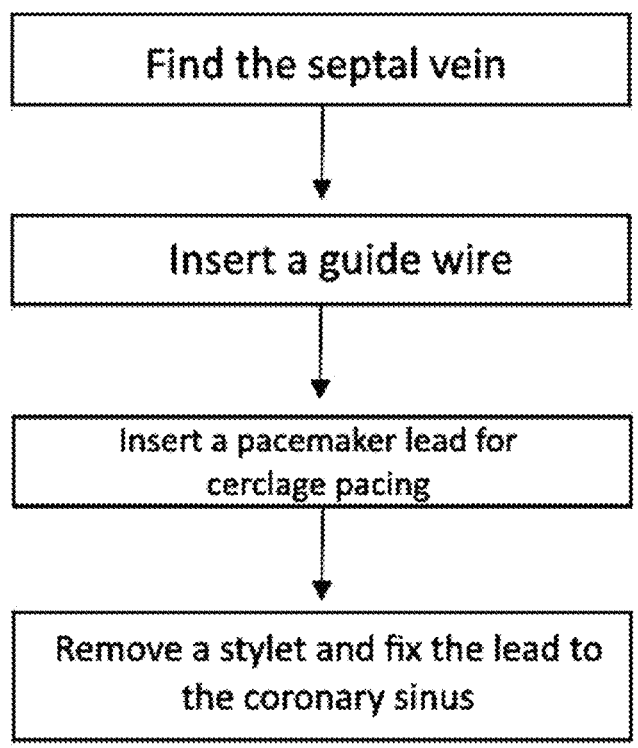
FIG. 8 is a flowchart showing an operation method using a lead according to an exemplary embodiment of the present invention.

FIG. 8 is a flowchart showing an operation method using a lead according to an exemplary embodiment of the present invention.

Figure 9A:
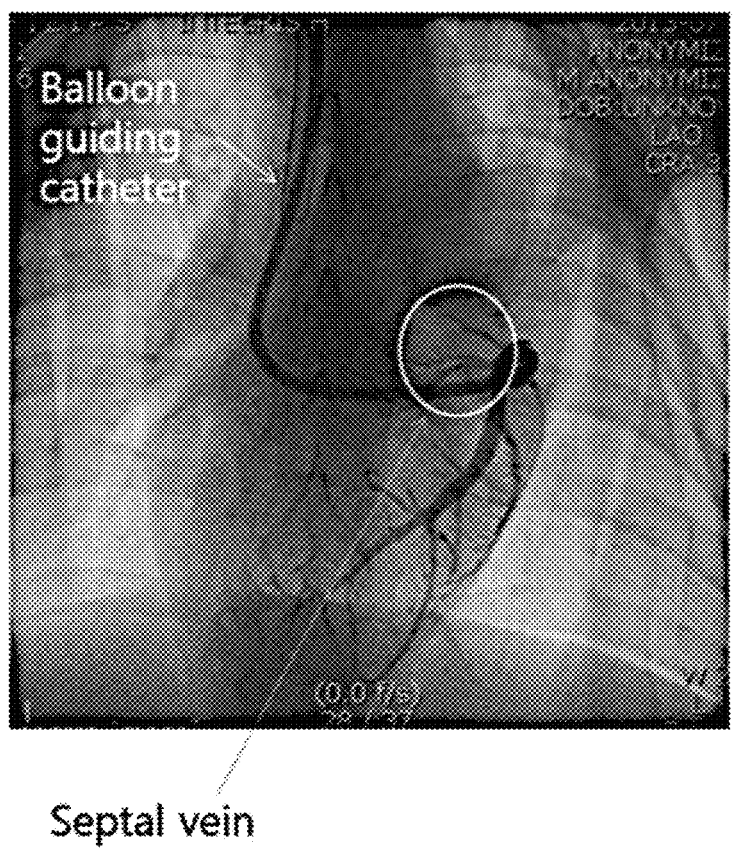
FIG. 9A is a picture showing a pressurized septal venogram when a coronary sinus is blocked by use of a balloon catheter.
Figure 9B:
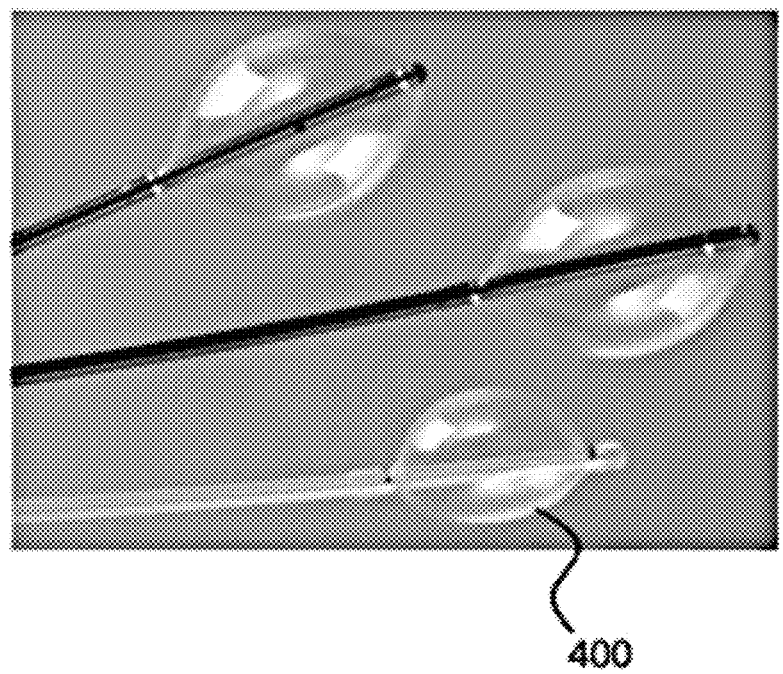
FIG. 9B is a view showing balloon catheters.

Referring to FIG. 8, in a method of performing an operation using a pacemaker lead for cerclage packing according to the present invention, a balloon tipped guiding catheter 400 is first inserted into the body of a patient, to check a septal vein. The balloon tipped guiding catheter 400 is a catheter formed with a balloon at an upper part thereof, as shown in FIG. 9B. After the catheter 400 is inserted through superior vein cava and the coronary sinus, external air is injected into the catheter 400 to inflate the balloon, thereby blocking the coronary sinus. According to this, the blood flow in the coronary sinus is blocked, causing pressure of the coronary sinus to be increased, thereby inflating the coronary sinus. Thereafter, a septal vein located at the interventricular septum is found from a pressurized venogram (refer to FIG. 9A).

In lieu of the balloon tipped guiding catheter 400, a catheter having one side to which a tip is coupled (not shown) is also available. The tip has a diameter similar to an inner diameter of the blood vessel and blocks the coronary sinus, being capable of increasing the pressure of the coronary sinus.

Then, the guide wire 200 is inserted into the superior vein cava, the coronary sinus, and the found septal vein. At this time, if a septal vein is not found, or the septal vein is not located at a position desired by the operator, the heart muscle can be perforated by inserting a perforating device thereinto. The perforating device is optional and is not necessarily required.

The lead 100 according to the present invention is inserted along the inserted guide wire 200.

Figure 10:
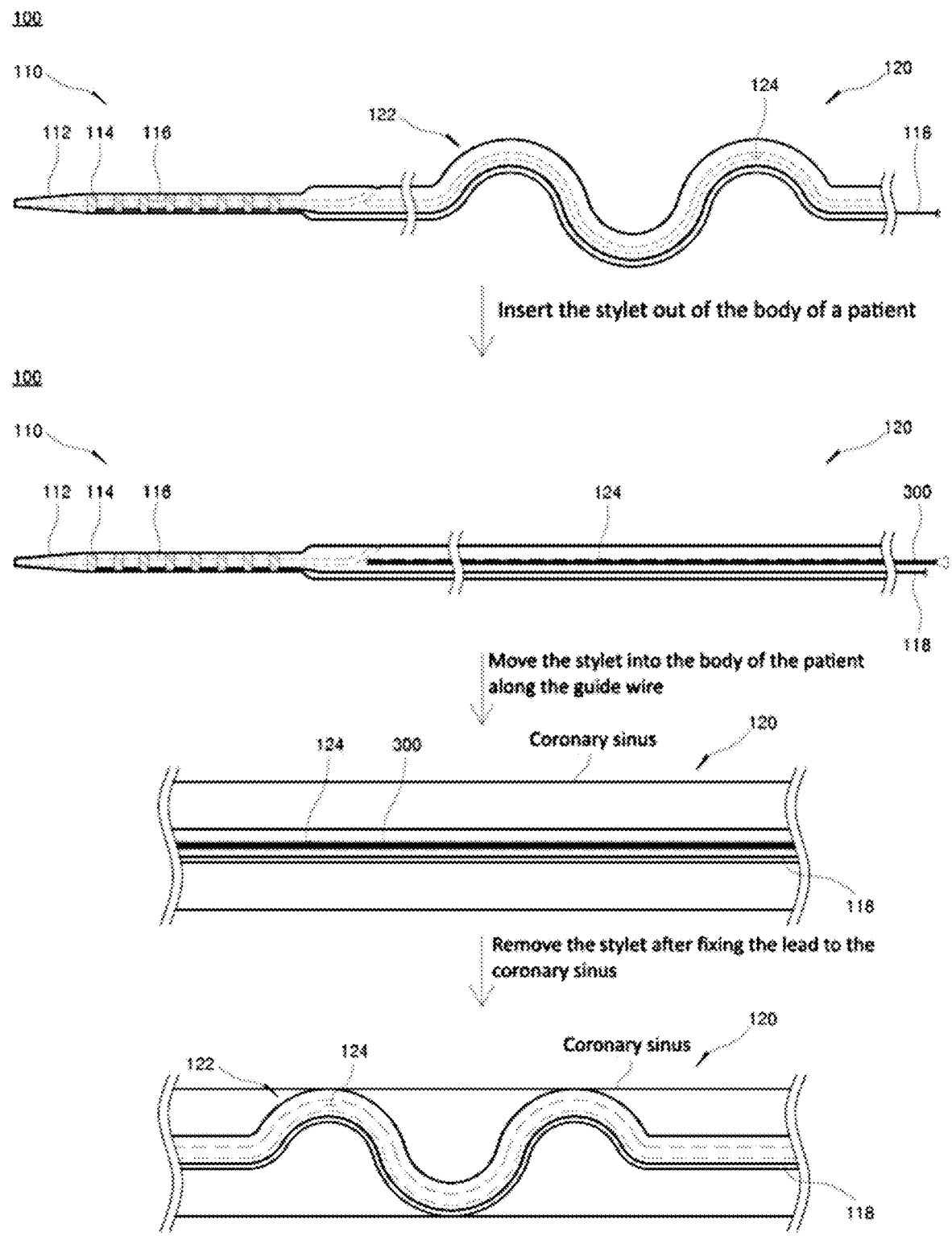
FIG. 10 is a flowchart showing an operation method using a lead according to an exemplary embodiment of the present invention.

FIG. 10 is a flowchart showing an operation method using a lead according to an exemplary embodiment of the present invention. Referring to FIG. 10, an operation will be explained below.

First, a lead 100 according to the present invention, prepared outside the body of a patient before a stylet 300 is inserted into the lead 100, is shown. The lead 100 is prepared to have a body fixing part 122 bent in a spiral or wave bent form, etc. Then, the lead 100 is prepared by inserting the stylet 300 into the lead outside the body of the patient, so that the body fixing part 122 is in a state of being spread. The lead 100 as prepared above is inserted into the body of the patient along the guide wire 200 inserted into the body of the patient earlier.

Next, it is shown that the lead 100 prepared in a straight line is inserted into the body of the patient and moves along the coronary sinus. The lead 100 according to the present invention includes the stylet 300, thereby enhancing pushability of the lead 100.

Last, the lead 100 moves along the guide wire 200 to cause the lead fixing part 110 to be fixed at the interventricular septum. If the stylet 300 is removed, the body fixing part 122 is recovered to the originally bent form in a wave or spiral form, etc. as shown therein and then fixed at the coronary sinus as bent.

According to this, there is an advantage that the lead 100 is not changed at the position once fixed. Also, as the lead 100 includes a plurality of electrodes 114, it is possible to find a position for electrical transmission suitable for each patient, without performing a re-operation to move the position of the lead 100, and efficiently transmit the electricity.

Figure 11:
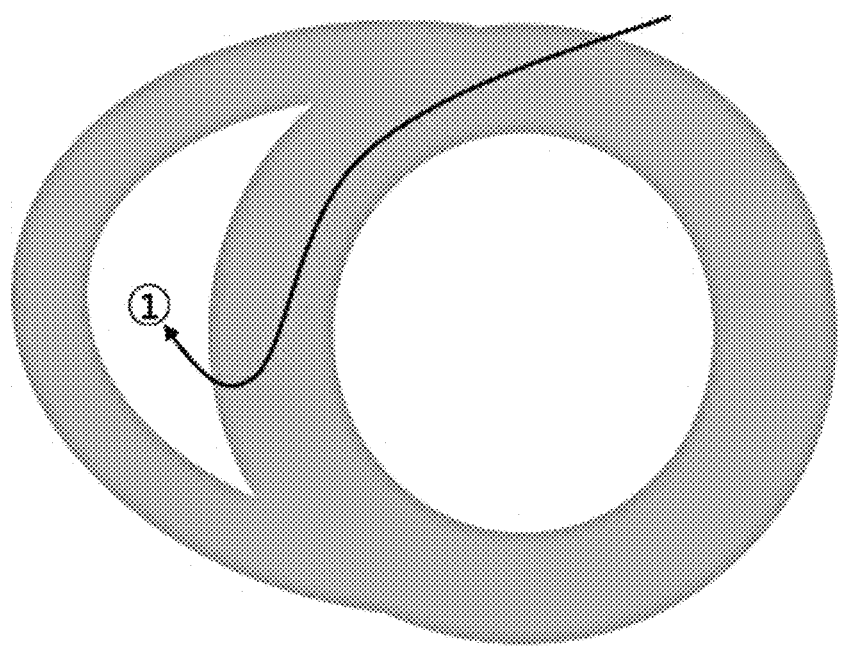
FIG. 11 is a schematic diagram showing a passage ① into which a guide wire is inserted in an experiment using a pacemaker lead according to the present invention.

FIG. 11 is a schematic diagram showing a passage ① into which a guide wire is inserted in an experiment using a pacemaker lead according to the present invention. A passage to insert the guide wire along the coronary sinus into the septal vein to pass through the interventricular septum is shown.

In this experiment, the lead according to the present invention is inserted along the passage through which the guide wire 200 is inserted.

Figure 12:
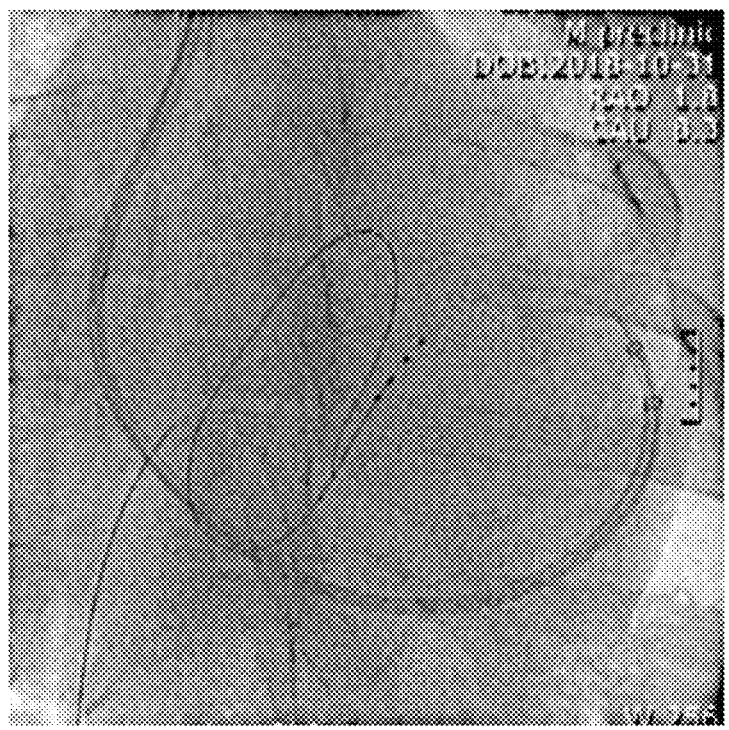
FIG. 12 is an X-ray picture showing a lead inserted through the passage ① of FIG. 11.

FIG. 12 is an X-ray picture showing a lead inserted through the passage ① of FIG. 11 and then fixed at the base of the interventricular septum.

Referring to FIG. 12, four bipolar electrodes are coupled to the pacemaker lead according to the present invention, wherein an interval between the electrodes is set 2 mm. The pacemaker lead is inserted into the superior vein cava, the coronary sinus, and the septal vein along the guide wire inserted through the passage ① shown in FIG. 11 and fixed at the basal interventricular septum.

Electrical transmission efficiency when the lead according to an exemplary embodiment of the present invention is fixed at the basal interventricular septum will be compared with electrical transmission efficiency when a lead is fixed at a position to fix the lead according to a conventional research.

As described above in the Description of the Related Art section, the positions at which the lead is fixed according to a conventional research include an RV apical pacing, an RV septal pacing, an LV epicardial pacing, an LV endocardial pacing, an LV apical pacing and an LV near apical pacing.

As seen in the picture of FIG. 12, among the four electrodes of the lead inserted into the body of the patient through the guide wire inserted in the direction of passage ① and fixed at the intra septal pacing, two electrodes are selected (second and third electrodes, second and fourth electrodes, first and third electrodes or first and fourth electrodes), to which electricity is transmitted, measuring QRS values, and after inserting the lead according to the conventional method, electricity is transmitted and QRS values are measured. Table 1 below indicates QRS values in the experiment.

TABLE 1

| Location | QRS (Unit: msec) |
| --- | --- |
| Self rhythm | 83 |
| RV septal pacing | 93 |
| RV apical pacing | 165 |
| Intra septal pacing(second and third electrodes) | 75 |
| Intra septal pacing(first and third electrodes) | 75 |
| Intra septal pacing(second and fourth electrodes) | 75 |
| Intra septal pacing(first and fourth electrodes) | 75 |

Referring to Table 1, when the lead was fixed at the basal interventricular septum in the direction of passage ①, all narrow QRS values were able to be obtained. To compare with the values of the comparative examples (the first to three locations in Table 1), excellent results are indicated. Where the electrodes are located in the interventricular septum, narrow QRS values having no relatively great difference are exhibited, without regard to which two electrodes are selected among the four electrodes. This indicates more excellent values than QRS where the lead is inserted according to the conventional method. However, if an electrode moves near to an internal membrane of the right ventricle or the external membrane of the left ventricle, a phenomenon that the QRS becomes long again is shown. This fact is interpreted to mean that an ideal position to fix the electrode is in the interventricular septum.

Accordingly, using the lead according to the present invention, the lead is fixed at the basal interventricular septum close to the His bundle, enabling efficient electrical transmission. As the lead according to the present invention includes a plurality of electrodes, electrical stimulus at several positions can be checked. Also, as the lead according to the present invention does not damage other tissues in the heart, the pacemaker lead can be inserted and fixed in a stable manner.

Although preferred embodiments of the present invention have been described for illustrative purposes, those skilled in the art will appreciate that various modifications, additions and substitutions are possible, without departing from the scope and spirit of the invention as disclosed in the accompanying claims. Accordingly, the exemplary embodiments as described above are for illustrative purposes and should not be construed without limitation thereto.

What is claimed is:

1. A method of performing intra-septal pacing in a patient's heart, comprising:
   having a pacemaker lead comprising:
   (a) a lead body comprising a body fixing part that has a straight configuration, but self-bends into a spiral or wave form;
   (b) a lead fixing part having a plurality of electrodes thereon;

(c) a channel for a stylet, inserting a stylet into the channel to make the body fixing part have a straight configuration;

inserting the pacemaker lead into the patient's body;

advancing the pacemaker lead into a coronary sinus of the patient's heart;

advancing the pacemaker lead to an interventricular septum of the patient's heart;

fixing the lead fixing part into the interventricular septum;

positioning the body fixing part inside the coronary sinus;

withdrawing the stylet from the pacemaker lead, thereby causing the body fixing part to self-bend into a spiral or wave form within the coronary sinus;

activating the electrodes to provide intra-septal pacing in the patient's heart.

2. The method of claim 1, wherein the body fixing part in spiral or wave form presses against the coronary sinus.

3. The method of claim 2, wherein the body fixing part comes into contact with two or three points at an inner wall of the coronary sinus.

4. The method of claim 3, wherein the stylet is stiffer at a proximal part than at a distal part.

5. The method of claim 2, wherein the stylet is stiffer at a proximal part than at a distal part.

6. The method of claim 1, wherein the position of the lead fixing part is between a His bundle and left ventricular septum of the patient's heart.

7. The method of claim 6, wherein the stylet is stiffer at a proximal part than at a distal part.

8. The method of claim 1, wherein the body fixing part has a spiral or wave form prior to insertion of the stylet into the channel.

9. The method of claim 8, wherein the stylet is stiffer at a proximal part than at a distal part.

10. The method of claim 1, wherein the stylet is stiffer at a proximal part than at a distal part.

* * * * *